(12) United States Patent
Rolla

(10) Patent No.: US 6,654,966 B2
(45) Date of Patent: Dec. 2, 2003

(54) FULLY COLLAPSIBLE HEADSET

(76) Inventor: José Maria Rolla, Perón 1219 - piso 3° "14", Buenos Aires (AR), (1038)

( * ) Notice: Subject to any disclaimer, the term of this patent is extended or adjusted under 35 U.S.C. 154(b) by 0 days.

(21) Appl. No.: 10/374,435

(22) Filed: Feb. 25, 2003

(65) Prior Publication Data

US 2003/0182713 A1 Oct. 2, 2003

(51) Int. Cl.⁷ .............. A42B 1/06; H04R 25/00
(52) U.S. Cl. ............. 2/209; 381/374; 381/383
(58) Field of Search .......... 2/209, 423; 128/866; 181/19; 381/383, 379, 378, 374, 370, FOR 149; 379/430

(56) References Cited

U.S. PATENT DOCUMENTS

| 375,594 | A | * | 12/1887 | Basch | 2/209 |
|---|---|---|---|---|---|
| 1,398,958 | A | * | 12/1921 | Basch | 2/209 |
| 1,571,471 | A | | 2/1926 | Galayda | |
| 3,272,926 | A | | 9/1966 | Falkenberg | |
| 3,682,268 | A | * | 8/1972 | Gorike | 181/129 |
| 4,404,434 | A | | 9/1983 | Pelt et al. | |
| 4,409,442 | A | * | 10/1983 | Kamimura | 381/383 |
| 4,571,746 | A | * | 2/1986 | Gorike | 2/209 |
| 4,930,148 | A | * | 5/1990 | Lee | 455/575.2 |
| 5,862,241 | A | * | 1/1999 | Nelson | 381/379 |
| 5,996,123 | A | * | 12/1999 | Leight et al. | 2/209 |
| 6,385,325 | B1 | * | 5/2002 | Nageno et al. | 381/374 |

FOREIGN PATENT DOCUMENTS

| DE | 741692 | | 9/1943 | | |
|---|---|---|---|---|---|
| GB | 1218086 | | 1/1971 | | |
| GB | 2130470 | A | * | 6/1984 | A41D/21/00 |
| JP | 59210790 | A | * | 11/1984 | H04R/1/10 |

* cited by examiner

*Primary Examiner*—Rodney M. Lindsey
(74) *Attorney, Agent, or Firm*—Emrich & Dithmar

(57) ABSTRACT

A fully collapsible headset assembly includes a headband portion formed by side arm members articulated together by a flexible hinge member. The flexible hinge member includes an elastic cam member, the force of which is released to maintain the assembly in either an operating or collapsed position, as desired. In the collapsed position, the tension of the cam member maintains a permanent pressure and the headband assembly forms a cavity in which the facing ear-cups are retained.

12 Claims, 8 Drawing Sheets

FULLY COLLAPSIBLE HEADSET

BACKGROUND OF THE INVENTION

The present invention relates to a headset assembly which, when mounted on the user's head, covers the user's ears to protect them from exterior noise or cold and to facilitate listening to sound signals. More particularly, the invention relates to a collapsible headset assembly having an elastic hinge assembly which biases the headset assembly to a folded collapsed position.

U.S. Pat. No. 1,571,471 discloses a headset in which the headband is unsuitable for earphones and does not bias the headset in a collapsible position. This is due to the fact that the headset is a flexible strap which does not form a structure capable of containing the headset in a biased collapsed position.

U.S. Pat. No. 3,272,926 discloses a headset with a hinge between the earphones and the headband member. However, the headband member is not hinged thereby preventing folding of the headset.

U.S. Pat. No. 4,404,434 discloses a headset having hinges which permit the cup assembly members to rotate into the concavity formed by the headband, but which does not permit hinging of the headband to a collapsed position. Therefore, the cup assemblies cannot be collapsed facing each other for their padded areas to be compressed and to reduce the occupied space. Moreover, the headband lacks a flexible hinge;

U.S. Pat. No. 4,571,746 discloses a headset with an intermediate hinge in the headband and in which the earphones or ear-pieces face each other when collapsed. However, the ear-pieces have a support connected to their back which limits their rotation capacity so that, when collapsed, they are outside the radial edge of the headband. Moreover, the headset lacks an elastic hinge member which biases the headband between folded or unfolded positions.

GB Patent 1,218,086 discloses a headset which includes hinged earphones which are collapsed within a channel in the headband. The inflexible headband is not hinged, but includes a channel which receives the ear-pieces therein.

DE Patent 741,692 discloses a headset which permits the hinged earphones to be collapsed into the cavity formed by the headband. However, the earphones cannot be collapsed facing each other so that a large cavity space is required. Moreover, the headband does not include a flexible hinge.

SUMMARY OF THE INVENTION

The present invention relates to a collapsible headset assembly which is adapted to mount onto a user's head to provide protection against exterior noise or cold and to facilitate listening to sound signals. The collapsible headset assembly includes a headband formed by side arms articulated by means of a flexible hinge member. The flexible hinge member includes an elastic cam which opposes closing and opening positions of the hinged headband. In the closed position, the headband forms a cavity which is structurally arranged to receive the ear-cups or ear-pieces therein.

One object of the present invention is to provide a collapsible ear-cup or ear-piece headset assembly wherein the side arms of the headband portion substantially enclose and receive the ear-pieces therein.

Another object of the present invention is to provide a collapsible headset assembly wherein the headband portion or member includes a hinge member which includes biasing means to predeterminely maintain the headband in its folded or opened positions. In the opened position, the biasing means of the hinge member provides a pressure that insures locking in the opened position.

One advantage of the present invention is that as the ear-cups are folded facing one other, the pressure supplied by the biasing means compresses the padded frames, thus reducing the volume or space occupied by the collapsed headset and ear-cups.

Still another advantage of the present invention is that as the headset assembly is in the collapsed position, the ear-cups are positioned to face each other so that the area which is applied to the user's head is protected during storage. This advantage is particularly important in the case of sound reception headsets, for example, of music, radio, and telephones, because in the folded, stored position, the components inside the ear-cup are protected due to the facing arrangement of the ear-cups.

A further advantage of the present invention is that the headset assembly includes ear-cup members which may be completely collapsed and stored in a pocket.

Another advantage of the present invention is that the headset assembly is fully collapsible, thus reducing volume and making packaging, transport and storage costs less costly.

Yet a further advantage of the present-invention is that the headset assembly may be worn under caps, hats, safety helmets, and military helmets, thereby replacing headsets which are commonly uncomfortable, bulky and difficult to put in place.

An additional advantage of the present invention is that the different component parts of the headset assembly may be easily replaced in case of breakage because it may be constructed using mainly plastic material, thus rendering it very light in weight.

Still an additional advantage of the present invention is that the plastic material used in constructing the headset assembly provides for an effective electric current insulation, which is very important in factories where there may be exposure to electric discharge on the user's head.

DESCRIPTION OF THE DRAWINGS

For the sake of clarity and understanding of the objects of the present invention, the present device is illustrated in different figures in which it has been represented in one of the preferred embodiments, by way of example and not by limitation:

FIG. 9 is a front view of the ear-cup member used to listen to sound signals in accordance with the present invention; and.

Figure 1:
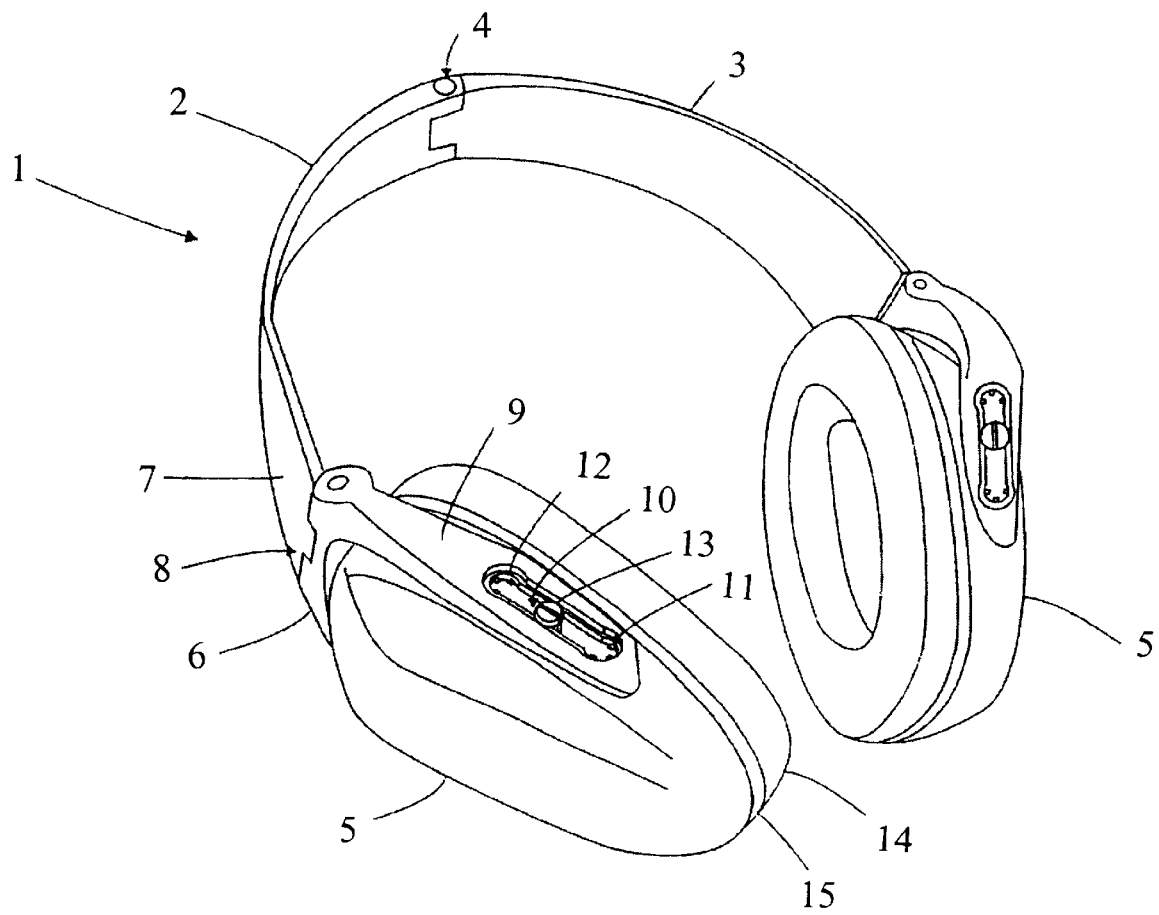
FIG. 1 is a perspective view of the collapsible headset member in accordance with the present invention.

REFERENCE NUMERALS IN THE DRAWINGS (1) Headset headband;
(2) First side arm member of the headband 1;
(2') External surface of the first side arm 2;
(3) Second side arm member of the headband 1;
(3') External surface of the second side arm 3;
(4) Flexible hinge assembly between proximal ends of the first and the second arm members;
(5) Ear-cup members;
(6) U-shaped forked members on which ear-cups are mounted;
(7) Distal ends of the side arms;
(8) Second hinge assemblies between the distal ends of the side arms and the forked members;
(9) Forked arms of forked members;
(10) Sliding runner for the third hinge portion;
(11) (12) Ends of runners;
(13) Third hinge assemblies between the ear-cup and the forked arm of the forked member;
(14) Padded frames members;
(15) Washer frame members;
(16) Coupling ledge;
(17) Coupling recess;
(18) Side portions surrounding the ledge on the sides;
(19) Hinge pin;
(20) Cam members;,
(21) Sliding tracks of the cams;
(22) Headband opening stops formed by the edge above the cam;
(23) Internal border of the sliding runner;
(24) Retentive members of the third hinge;
(25) Sliding border;
(27) Perimeter fitting between ear-cups, bases and padded frames;
(28) Filling composition;
(29) Coupling border;
(30) Connector channel;
(31) Fastening member;
(32) Wire;
(33) (34) Sound absorption cells.

DESCRIPTION OF THE PREFERED EMBODIMENT

As shown in FIG. 1, the collapsible headset assembly in accordance with the present invention comprises a headband 1, formed by two side arm members 2 and 3, coupled together by means of a flexible hinge assembly 4 at their proximal ends thereof. The headband 1 is substantially flat and curved in shape. The headset assembly includes ear-cup members 5 connected to the headband 1 by means of U-shaped forked members 6, the base of which is hingedly connected to the distal ends 7 of the headband 1, thereby providing a second elastic hinge assembly 8 which provides for the folding and unfolding movements of the headband 1 of the headset in accordance with the present invention.

Figure 5:
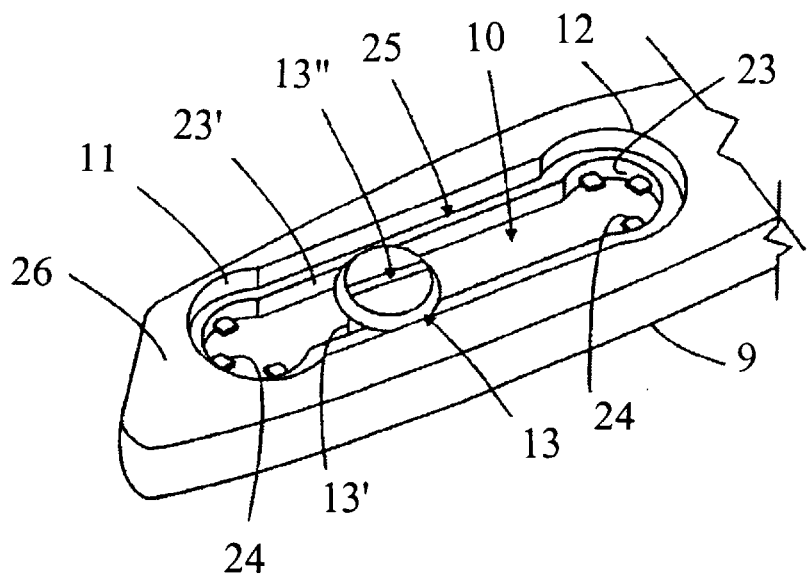
FIG. 5 is a perspective view of the ear-cup hinge member engaged with the sliding runner in accordance with the present invention.

Each U-shaped forked member 6 includes forked arms 9 which include a sliding runner portion 10, of which the ends. 11 and 12 thereof are widened in substantially circular shape, as shown in FIG. 5. The head of the third hinge portion 13, which is part of the ear-cup member 5, extends through the runner 10 and is held therein. This enables the ear-cup member 5 to slide along the forked arms 9 of forked member 6 between the ends 11 and 12 of the sliding runner 10, to permit the relative positioning of the ear-cups 5 to the user's head during usage and to permit the relative position of the ear-cups when the headset assembly is in the collapsed position, as shown in FIG. 3.

Figure 6:
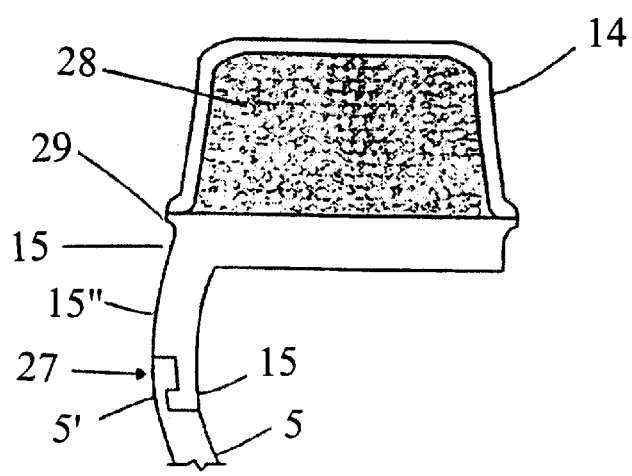
FIG. 6 is a cross sectional view of the ear-cup in accordance with the present invention.

Although in FIG. 1 only one of the forking arms 9 of the U-shaped member 6 is shown, the other forked arm 9 is hidden in this figure behind the corresponding ear-cup 5, with the hidden forked arm 9 having identical characteristics and structure to the forked arm 9, as shown in FIG. 1. In FIGS. 1 and 6 it is also shown that in the contact area with the user's ears, the ear-cups 5 have annular padded frame members 14 coupled to the ear-cups by washer frame members 15.

Figure 2:
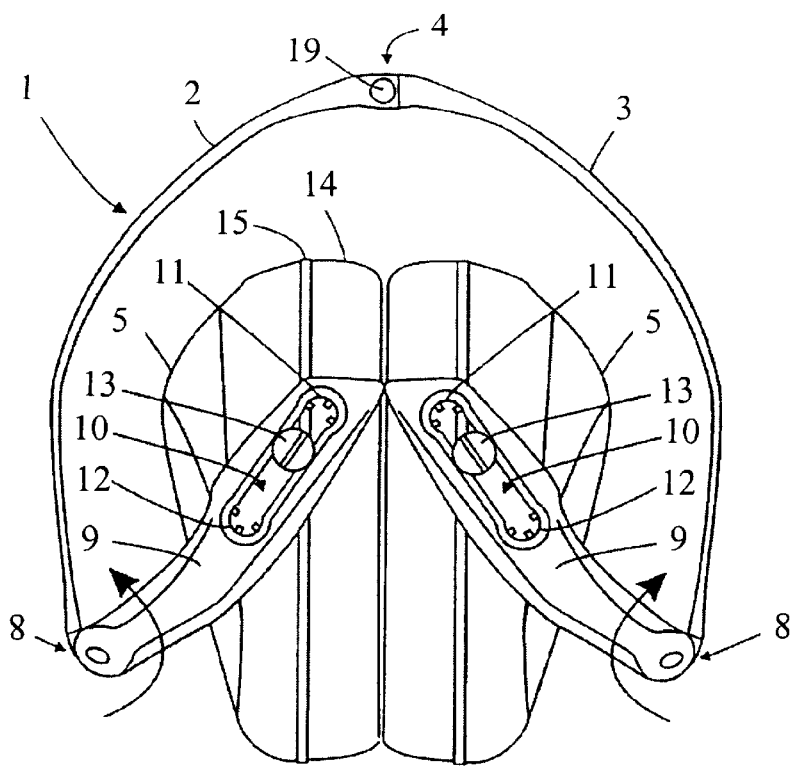
FIG. 2 is a side view of the present invention illustrating the headset member with its facing ear-cup members at the start of the folding operation.
Figure 3:
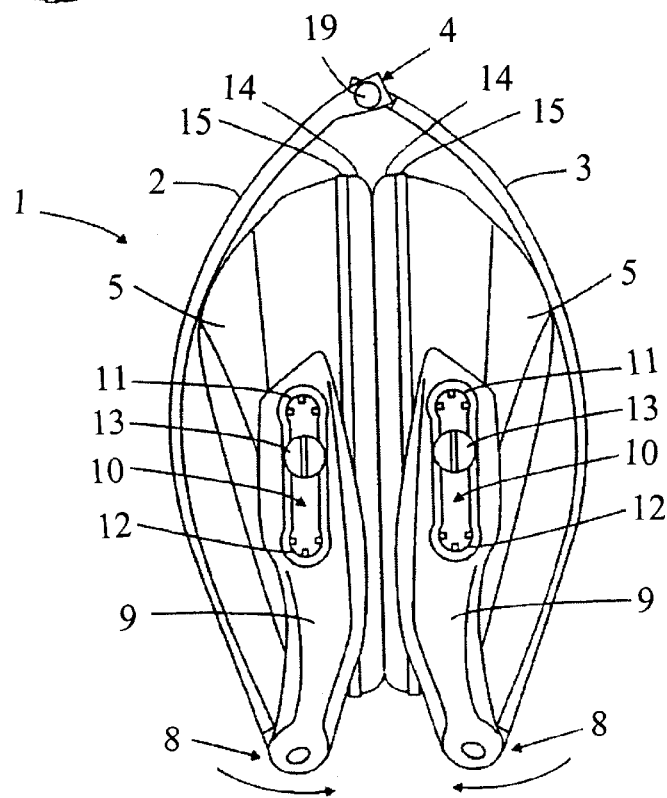
FIG. 3 is a side view of the present invention showing the headset member in the collapsed position.

FIGS. 2 and 3 illustrate the sequence of movements between the forked members 6 and the side arm members 2 and 3 of the headband 1. In FIG. 2, it is illustrated that when the second hinge assembly portion 8 is actuated, according to the distance traveled as shown by the arrows, the ear-cup members 5 are arranged in alignment in the space defined between the side arms 2 and 3. At the same time, the ear-cup members 5 slide within the runner 10 of the forked arms 9 of the forked member 6, so that they are placed in the most suitable position or alignment for the final folding or collapse of the headset, as shown in FIG. 3.

Once the ear-cup members 5 are arranged in alignment, as shown in FIG. 2, side arm members 2 and 3 of the headband 1 are collapsed in the direction shown by the corresponding arrows of FIG. 3, thus allowing a considerable reduction in size or space that is occupied by the headset assembly, due to its complete folding. Besides, the annular padded frame members 14 are compressed and occupy a minimum space thereby contributing to the final reduction in size of the collapsed headset assembly.

Both the flexible hinge assembly 4 between the proximal ends of side arms 2 and 3 of the headband 1 and the second hinge assembly 8 of the forked U-shaped members 6 allow for a fast and firm folding and unfolding of the headset assembly, while holding and maintaining the headset in each case in a stable and secure operating or collapsed position.

Figure 4:
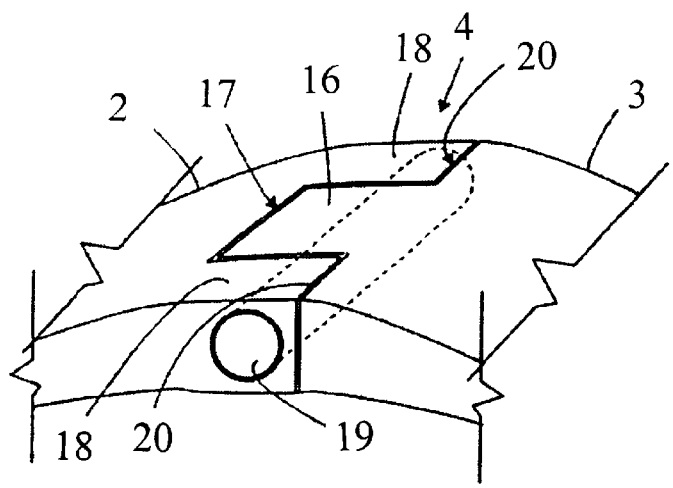
FIG. 4 is a perspective view of the present invention illustrating the flexible hinge member when the headband is in the open or operating position.
Figure 4A:
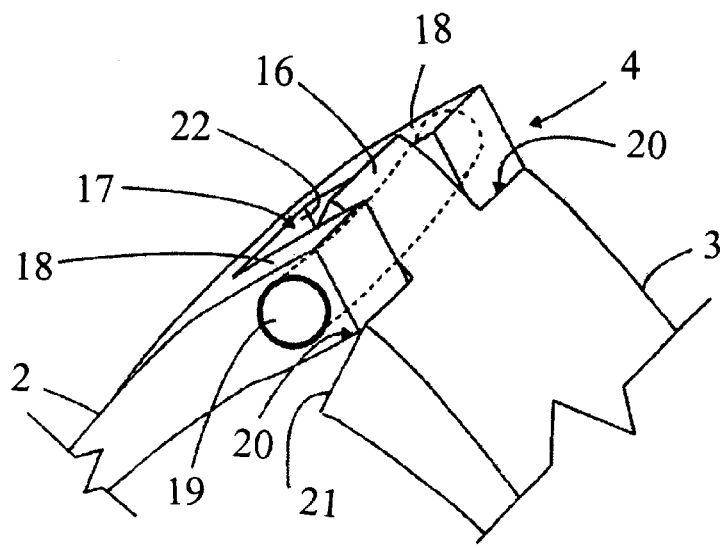
FIG. 4a is a perspective view of the present invention illustrating the flexible hinge member when the headband is in the collapsed position.

FIGS. 4 and 4a illustrate the flexible hinge assembly 4 between the proximal ends of side arms 2 and 3. The hinge assembly 4 is similar to the second hinge assemblies 8 between the opposing or distal ends 7 of said side arm members 2 and 3 and the forked members 6, as shown in FIG. 1. The flexible hinge assembly 4 includes a coupling ledge member 16 which projects from the second side arm 3 and which fits in a coupling recess 17 of the first side arm 2 of the headband 1, with the recess 17 being defined between side extension portions 18. A hinge pin 19 runs through the ledge member 16 and the side extension portions 18. The ledge member 16, the coupling recess 17 and the side extension portions 18 are structurally arranged so that an elastic relationship is established between side arm members 2 and 3 of the headband 1. This relationship is due to the fact that the lower borders of the ledge 16 and of the side portions 18 constitute cam members 20 which slide along the sliding tracks 21 to provide the forced mobility or biasing of the elastic or flexible hinge assembly 4.

Figure 4B:
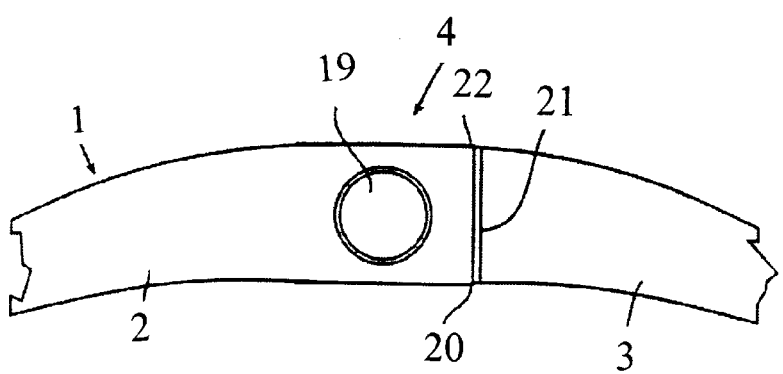
FIG. 4b is a side view of the present invention illustrating the flexible hinge member when the side arms of the headband are in the open or operating position.
Figure 4C:
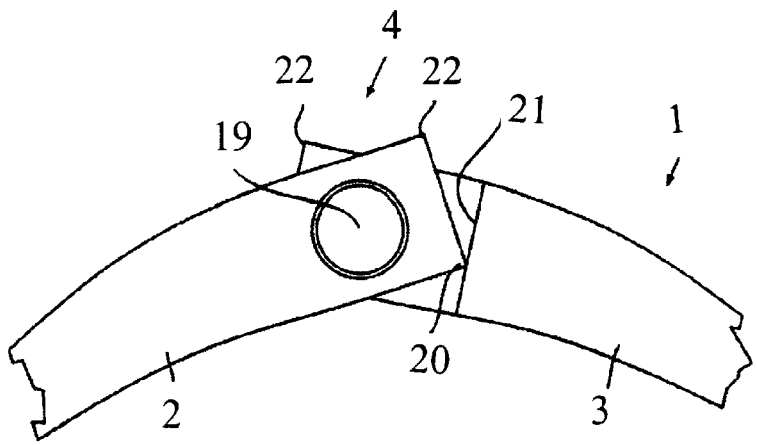
FIG. 4c is a side view of the flexible hinge member illustrating the cam tension between the side arms of the headband during movement of the hinge member between the operating and the collapsed positions.
Figure 4D:
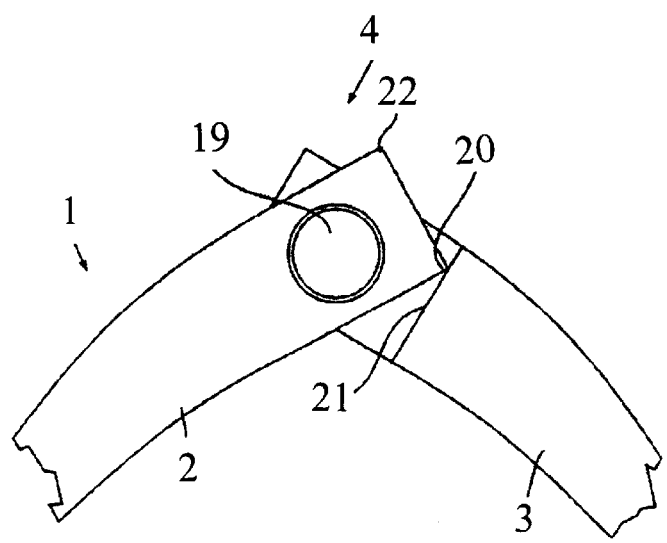
FIG. 4d is a side view of the flexible hinge member illustrating the cam tension between the side arms of the headband when the headband is in the collapsed position.

As shown in FIGS. 4, 4a, 4b, 4c and 4d, the forced mobility of the cam members 20 releases the tension to two opposing positions: a first end opening or operating position, corresponding to the unfolded headset, as shown in FIGS. 1 and 4b, and a second end position corresponding to the collapsed position, as shown in FIGS. 4a and 4d. The release of the cam member 20 between both positions drives the opening and folding movements of the headband 1. The tension provided by elastic cam member 20, as shown in FIG. 4c, may bias the headband 1 to either the open or collapsed positions, as desired.

The opening limit is set by stops 22 formed by the upper borders of the recess 17 and the ledge 16. The sliding of the cam members 20 along sliding tracks 21 takes place both between the ledge 16 and the recess 17 and between side portions 18 and the sides of ledge 16. The sequential folding of the ear-cups 5, articulated on the forked member 6, permits arms 2 and 3 of the headband 1 to be folded too, in a synchronized way, taking advantage of the space and attaining the maximum folding of the headset.

FIG. 5 shows that the ends 11 and 12 of sliding runners 10 of the arms 9 of U-shaped member 6 have an internal border 23 from which retentive members 24 project. These means 24 are elastically deformable to allow the entrance of the head of the third hinge assembly 13.

Along runner members 10 there is a sliding border 25 to support and guide the head of the third hinge assembly 13. The internal border 23 defined between ends 11 and 12 of runner members 10 acts as a guide for the body of the third hinge assembly 13.

In FIG. 6 it is shown that on a perimeter border of ear-cup members 5, there is a base 15, preferably made of a body of at least semi-rigid material detachably coupled by means of a perimeter fitting 27, formed by complementary recesses and ledges.

The padded frame members 14 comprise an external laminated material and a foamy filling composition 28, such as polyurethane foam, and are welded, using, for example, heat or ultrasonic welding, directly on the internal and/or external borders of a coupling border 29 of the washer frame member 15, said washer 15 and said padded frame 14 forming a set, as shown in FIG. 6.

Figure 7:
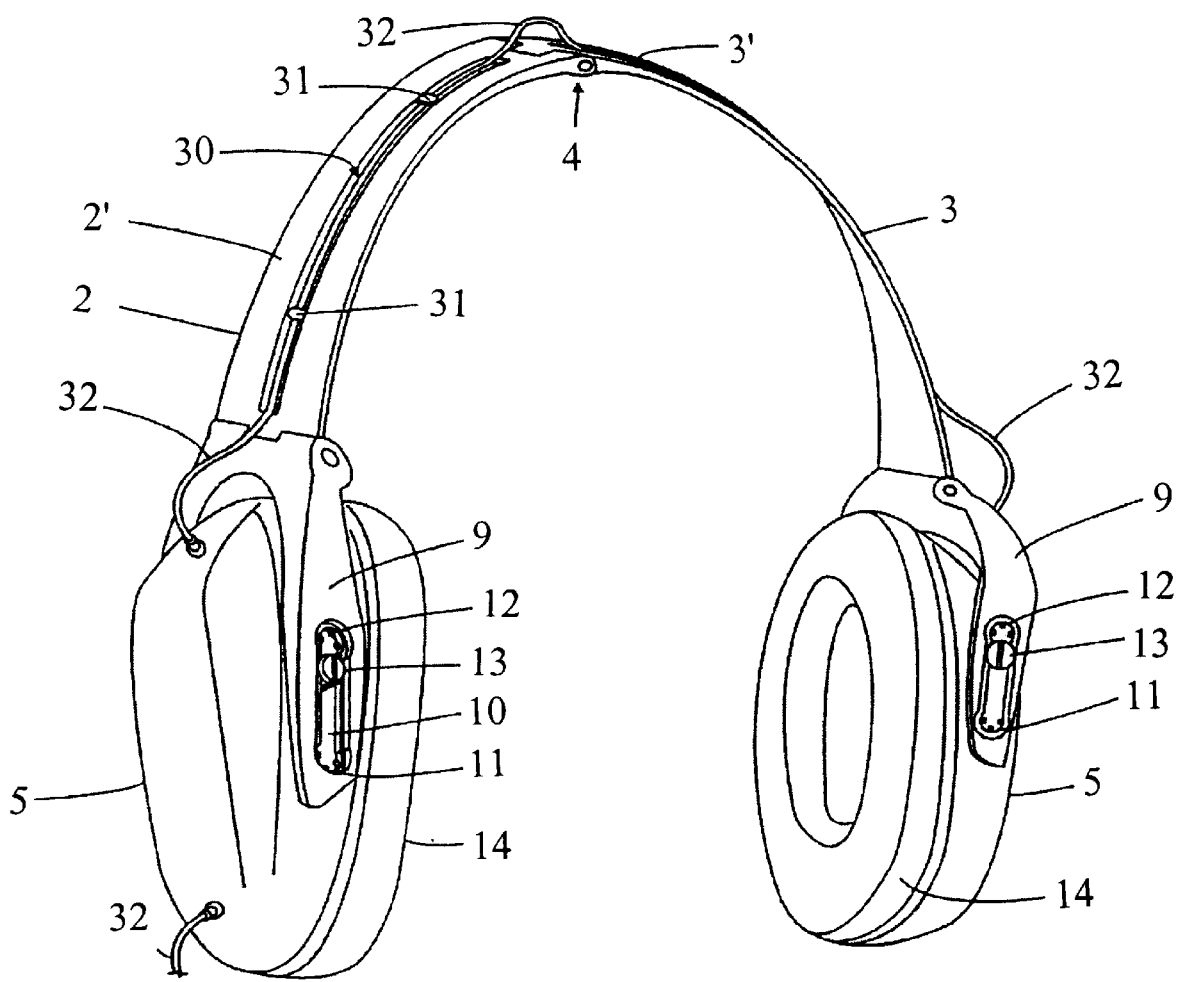
FIG. 7 is a perspective view of the headset for use with an embodiment used to listen to sound signals.

In an alternative embodiment of the present invention, as shown in FIG. 7, side arms 2 and 3 of the headband 1 have external surfaces 2' and 3', respectively, where there is a connector channel 30 with electroacoustic transducers incorporated to the headset to permit use of listening to music or radio communication. This channel 30 has fastening member 31 to retain the wire 32 within the channel 30.

Figure 8:
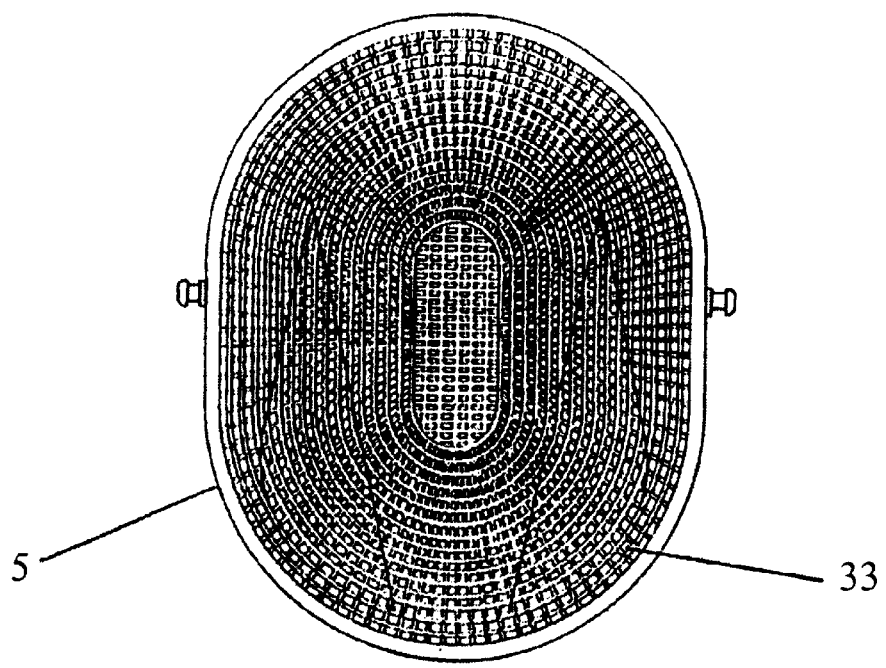
FIG. 8 is a front view of the ear-cup member in an embodiment in which it is used as noise protection.
Figure 8A:
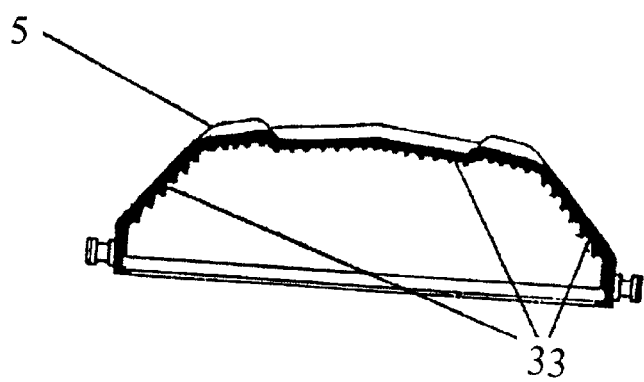
FIG. 8a is a cross sectional view of the ear-cup member shown in FIG. 8.
Figure 9:
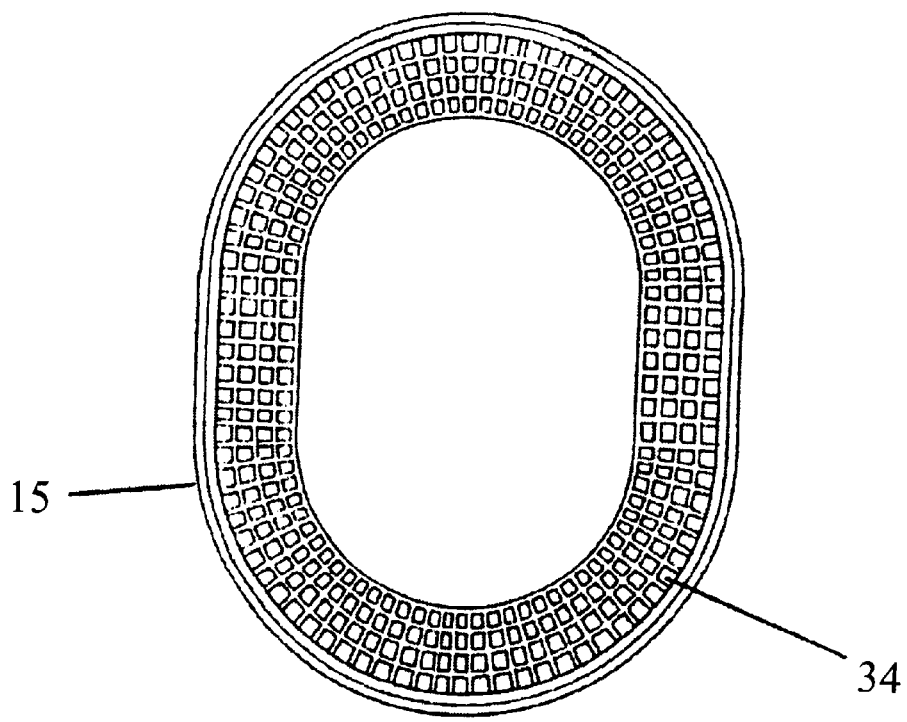
Figure 9A:
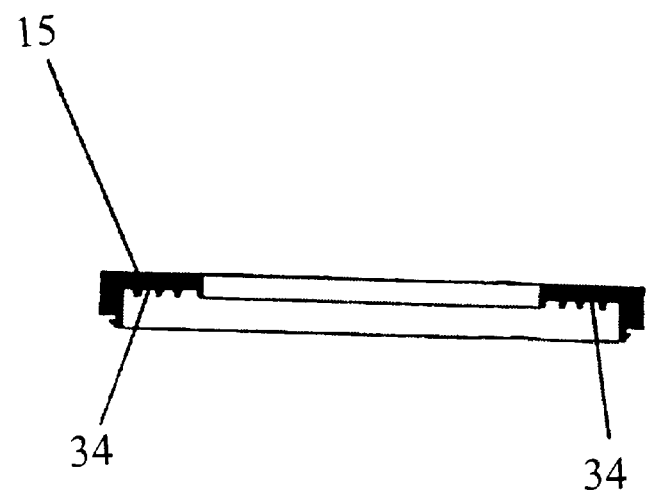
FIG. 9a is a cross sectional view of the ear-cup member shown in FIG. 9.

FIGS. 8 and 8a illustrate a particular embodiment of the ear-cup members 5 of the headset of the present invention, wherein on the internal surface of each of said ear-cup members 5 there are a plurality of sound absorption cells 33 regularly spaced, which may have different shapes, sizes and depth. FIGS. 9 and 9a show a particular embodiment of washers 15, in which the internal surface of said washers also has a plurality of sound absorption cells 34. The purpose of cells 33 and 34 is to protect the user's ears from the high level of noise which might be in the environment during use of the headset assembly.

What is claimed is:

1. A headset assembly which is adapted to engage a user's head and ears to provide noise protection, cold protection or listening to sound signals; including in combination:

ear-cup members for engagement with user's ears;

a headband portion comprised of a pair of side arm members, each side arm member having a proximal end and a distal end, with said side arm members coupled together at their proximal end by a first hinge assembly, with each of said distal ends having a second hinge assembly coupled to a support member, with said support member structurally arranged to receive and mount said ear-cup members;

wherein said ear-cup members are operatively connected to said support member by a third hinge assembly; and whereby said first hinge assembly permits said side arm members to articulate between a collapsed position and an operating position, with said first hinge assembly including a cam member which selectively biases said headband portion into and in said collapsed position.

2. The headset assembly in accordance with claim 1, wherein said first hinge assembly includes a ledge and recessed type of hinge coupling between said proximal ends of said side arm members to provide a biasing cam action to retain said headband portion in said collapsed position.

3. The headset assembly in accordance with claim 2, wherein said first hinge assembly further includes a hinge pin in said proximal ends of said side arm members for pivotally hinging said ledge and recessed type of hinge coupling together.

4. The headset assembly in accordance with claim 1, wherein said first hinge assembly is comprised of an elastic cam member formed by at least a hinge pin and at least a ledge formed at the proximal ends of said side arm members, with said ledge contacting in a forced way a recess at the proximal end of the opposing side arm member.

5. The headset assembly in accordance with claim 1, wherein said first hinge assembly includes an elastic cam member positioned at the proximal ends of said side arm members and ledges which are structurally arranged to be received by recesses located at the end of the opposing side arm member.

6. The headset assembly in accordance with claim 1, wherein said headband portion is comprised of a plastic material.

7. The headset assembly in accordance with claim 1, wherein said side arm members are curved so that they complement each other to form a folding cavity structurally arranged to enclose both ear-cups therein when in said collapsed position.

8. The headset assembly in accordance with claim 1, wherein said ear-cup members include padded frames which are elastically compressible when in said collapsed position.

9. The headset assembly in accordance with claim 1, wherein said support members of said second hinge assembly are U-Shaped forked members which are operatively connected to respective ear-cups by said third hinge assembly.

10. The headset assembly in accordance with claim 9, wherein each of said U-shaped forked members have leg portions which define a channel therein which is structurally arranged to cooperate with said third hinge assembly to provide maximum folding when in said collapsed position.

11. The headset assembly in accordance with claim 1, wherein said second hinge assembly includes a cam member comprised of ledges formed in the articulated contact area between said support members and said distal ends of said side arm members.

12. The headset assembly in accordance with claim 1, wherein said third hinge assembly is positioned between said ear-cup members and said support members of said second hinge assembly.

* * * * *